United States Patent
Brahm

(10) Patent No.: US 11,167,061 B1
(45) Date of Patent: Nov. 9, 2021

(54) REPAIR OF TYMPANIC MEMBRANE USING HUMAN BIRTH TISSUE MATERIAL

(71) Applicant: BioDlogics LLC, Cordova, TN (US)

(72) Inventor: Timothy R. Brahm, Germantown, TN (US)

(73) Assignee: BioDLogics LLC, Cordova, TN (US)

( * ) Notice: Subject to any disclaimer, the term of this patent is extended or adjusted under 35 U.S.C. 154(b) by 0 days.

(21) Appl. No.: 15/889,310

(22) Filed: Feb. 6, 2018

Related U.S. Application Data

(62) Division of application No. 15/299,618, filed on Oct. 21, 2016, now Pat. No. 9,919,078, which is a division of application No. 14/194,907, filed on Mar. 3, 2014, now Pat. No. 9,498,327.

(60) Provisional application No. 61/772,688, filed on Mar. 5, 2013.

(51) Int. Cl.
- *A61L 27/36* (2006.01)
- *A61F 2/18* (2006.01)
- *A61F 2/00* (2006.01)

(52) U.S. Cl.
CPC ........ *A61L 27/3604* (2013.01); *A61F 2/0095* (2013.01); *A61F 2/18* (2013.01); *A61L 27/3641* (2013.01); *A61L 27/3687* (2013.01); *A61L 27/3691* (2013.01); *A61F 2240/001* (2013.01); *A61L 2430/14* (2013.01)

(58) Field of Classification Search
None
See application file for complete search history.

(56) References Cited

U.S. PATENT DOCUMENTS

| | | | |
|---|---|---|---|
| 4,361,552 A | 11/1982 | Baur, Jr. | |
| 5,607,590 A | 3/1997 | Shimizu | |
| 5,916,266 A | 6/1999 | Yui et al. | |
| 8,105,634 B2 | 1/2012 | Liu et al. | |
| 9,498,327 B1 * | 11/2016 | Brahm | A61F 2/18 |
| 9,919,078 B1 * | 3/2018 | Brahm | A61F 2/18 |
| 2001/0053839 A1 | 12/2001 | Noishiki | |
| 2007/0031471 A1 | 2/2007 | Peyman | |
| 2007/0038298 A1 * | 2/2007 | Sulner | A61F 2/18 |
| | | | 623/10 |
| 2009/0208551 A1 | 8/2009 | Kim | |
| 2011/0129520 A1 | 6/2011 | Bogdansky | |
| 2011/0189301 A1 | 8/2011 | Yang | |
| 2014/0052247 A1 | 2/2014 | Daniel | |

FOREIGN PATENT DOCUMENTS

WO WO-2012112441 A1 * 8/2012 ............. A61P 27/02

OTHER PUBLICATIONS

Lyons, G.D., et al., Morphologic Analysis of Tympanic Membrane Grafts, The Laryngoscope 87 (1977) pp. 1705-1709. (Year: 1977).*

* cited by examiner

*Primary Examiner* — Dominic Lazaro
(74) *Attorney, Agent, or Firm* — Barnes & Thornburg LLP

(57) ABSTRACT

A tympanic construct fabricated from at least one amniotic membrane, at least one chorionic membrane, or at least one amniotic membrane and at least one chorionic membrane obtained from human birth tissue is provided. Methods of preparing a tympanic construct, methods of repairing tympanic membrane defects and surgical sites, as well as kits for the same are also provided.

10 Claims, 2 Drawing Sheets

REPAIR OF TYMPANIC MEMBRANE USING HUMAN BIRTH TISSUE MATERIAL

CROSS-REFERENCE TO RELATED APPLICATIONS

This application is a divisional application of U.S. patent application Ser. No. 15/299,618, filed Oct. 21, 2016, which is a divisional application of U.S. patent application Ser. No. 14/194,907, now U.S. Pat. No. 9,498,327, filed Mar. 3, 2014, which claims priority to U.S. Provisional Patent Application No. 61/772,688 filed Mar. 5, 2013, the contents of which are each incorporated herein in their entirety.

FIELD OF THE INVENTION

The present invention is directed to a tympanic construct fabricated from at least one amniotic membrane, at least one chorionic membrane, or at least one amniotic membrane and at least one chorionic membrane obtained from human birth tissue. The present invention is further directed to methods of preparing a tympanic construct, methods of repairing tympanic membrane defects and surgical sites, as well as kits for the same.

BACKGROUND OF THE INVENTION

The first component of the middle ear to receive sound waves is the tympanic membrane, also known as the eardrum. Sound waves striking the tympanic membrane are transmitted through a series of bones (e.g., malleus, incus and stapes) to the cochlea, where the sound waves are sensed and processed.

Tympanic membrane deformities, such as perforations, interfere with the transmission and perception of sound. Perforations are usually caused by trauma or infection. Middle ear infections can cause spontaneous rupture (tear) of the eardrum, resulting in a perforation. A hole in the tympanic membrane may also be caused by surgical procedures, e.g., a small hole may remain in the eardrum after a previously placed pressure equalization tube either falls out or is removed by the physician.

Repair of tympanic membrane perforations is accomplished in a procedure known as tympanoplasty or myringoplasty. Generally, in tympanoplasty or myringoplasty, the hole in the tympanic membrane is repaired by means of a graft. Typical graft materials include natural materials such as temporalis fascia, tragal perichondrium, skin, periosteum, loose overlay tissue, fat, vein tissue, human amniotic membrane, and homologous dura; and non-natural materials such as silastic, paper and teflon sheets. Such typical graft materials used in these procedures, however, may cause further ear infection, loss of hearing, tinnitus, facial paralysis, or hematoma.

Thus, there exists a need for safe and effect materials and techniques to repair defects of the tympanic membrane.

SUMMARY OF THE INVENTION

The present invention is generally directed to methods and compositions for repair of tympanic membranes.

According to one aspect, a tympanic construct is provided. The tympanic construct includes at least one amniotic membrane, or at least one chorionic membrane, or at least one amniotic membrane and at least one chorionic membrane. The membrane(s) is/are treated with at least one alcohol composition followed by terminal sterilization to form a tympanic construct. According to one embodiment, the alcohol composition comprises from about 90% to about 100% ethanol. According to one embodiment, the terminal sterilization is gamma irradiation or electron beam irradiation.

According to another aspect, a method of preparing a membrane for a tympanic construct is provided. The method includes the steps of:

(a) obtaining amniotic membrane, chorionic membrane, or both amniotic and chorionic membrane from a seronegative, healthy human via Cesarean section or vaginal delivery;

(b) immersing the membrane in a basin containing a sterile saline solution;

(c) agitating the basin to liberate excess blood and fluids from the membrane;

(d) rinsing the membrane with a sterile saline solution;

(e) covering the membrane with a substrate on both the fetal membrane side and the maternal membrane side;

(f) optionally, immersing the membrane in an alcohol composition;

(g) optionally, rinsing the membrane with a sterile saline solution;

(h) optionally, soaking the membrane in a sterile saline solution;

(i) immersing the membrane in an alcohol composition for a period of from about 24 hours to about 384 hours;

(j) removing the substrate from both the fetal membrane side and the maternal membrane side;

(k) spreading the membrane on a flat, dry and sterile surface;

(l) allowing the membrane to air dry completely at ambient temperature for a period of up to three hours;

(m) cutting the membrane to a predetermined size; and (n) placing the fetal side of the membrane directly onto a pre-cut substrate to form a tympanic construct.

According to one embodiment, the method further includes the steps of packaging the tympanic construct in a concentration of ethanol and terminally sterilizing the packaged tympanic construct using irradiation. According to one embodiment, the method further includes the steps of packaging the tympanic construct in a dry state and terminally sterilizing the packaged tympanic construct using irradiation. According to one embodiment, the method further includes the step of removing the chorionic membrane via blunt dissection and discarding the chorionic membrane. According to one embodiment, the method further includes the step of placing the membrane in sterile saline solution for a period of up to about five days between steps (a) and (b). In such an embodiment, the sterile saline solution includes from about 0.9% to about 20% NaCl. According to one embodiment, the sterile saline solution in step (b) includes from about 0.9% to about 20% NaCl. According to one embodiment, the sterile saline solution in steps (d) and (g) each include from about 0.9% to about 20% NaCl, and the rinse steps (d) and (g) are conducted for a maximum time period of five minutes. According to one embodiment, the sterile saline solution in step (h) includes from about 0.9% to about 20% NaCl, and the soak in step (h) is conducted for a maximum period of about 35 minutes. According to one embodiment, the alcohol composition in steps (f) and (i) includes from about 90% to about 100% ethanol. According to one embodiment, the alcohol composition in steps (f) and (i) includes 95.5% ethanol. According to one embodiment, the alcohol composition in steps (f) and (i) includes 100% ethanol.

According to one embodiment, the method further includes the step of treating the membrane with an oxidizer between steps (a) and (b). According to one embodiment, the oxidizer is hydrogen peroxide and the step of treating the membrane further includes the steps of:

(a) rinsing the membrane with about 120 ml of sterile isotonic solution per gram of membrane for a time period of up to about ten minutes;

(b) treating the membrane with about 60 ml of hydrogen peroxide per gram of membrane for a time period of up to about ten minutes; and (c) rinsing the membrane with about 120 ml of sterile isotonic solution per gram of membrane for a time period of up to about ten minutes.

According to one aspect, a tympanic construct produced by the aforementioned methods is provided. According to one embodiment, the ethanol residual levels determined by gas chromatography are not detected at the corresponding minimum report limit.

According to one aspect, a method of treating a tympanic membrane defect is provided. The method includes the steps of preparing a tympanic construct as provided herein and contacting the tympanic membrane defect with the tympanic construct. According to one embodiment, the tympanic membrane defect is a perforation, tear, abrasion, rupture, or puncture in the tympanic membrane. According to one embodiment, the method further includes the step of hydrating the tympanic construct prior to placement.

According to one aspect, a method of treating a tympanic membrane surgical site is provided. The method includes the steps of preparing a tympanic construct as provided herein and contacting the tympanic membrane surgical site with the tympanic construct.

According to another aspect, a kit for use by a surgical professional is provided. According to one embodiment, the kit includes one or more packaged and sterilized tympanic constructs as provided herein. The kit may further include at least one set of instructions.

DETAILED DESCRIPTION OF THE INVENTION

Figure 1:
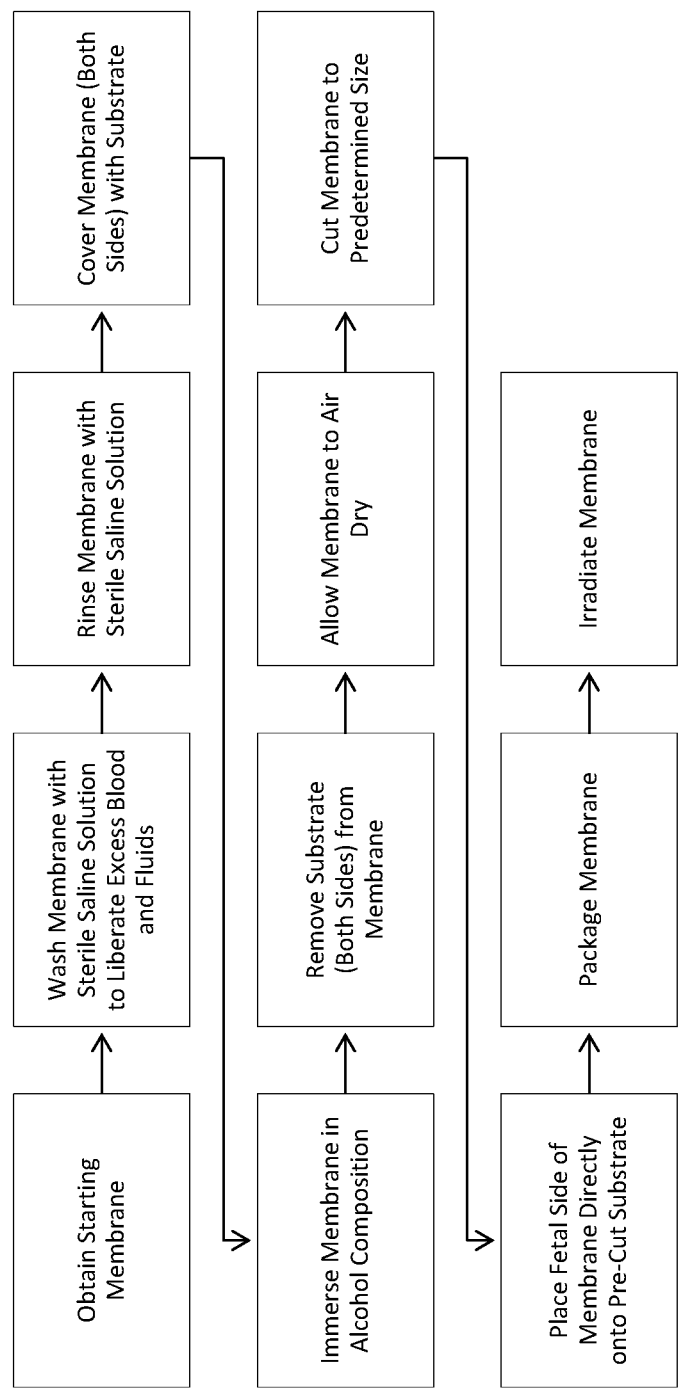
FIG. 1 illustrates a method of preparing a tympanic construct according to one embodiment.

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used herein, and in the appended claims, the term "construct" refers to a patch, graft, or other material embodiment suitable for contacting the tympanic membrane or surrounding tissue.

As used herein, and in the appended claims, the terms "optional" or "optionally" mean that the subsequently described event or circumstance can or cannot occur. For example, the phrase "optionally soaking the membrane" means that the soaking step may or may not be performed.

As used herein, and in the appended claims, the term "human birth tissue" includes, but is not limited to, elements of the placental organ such as, for example, the placental globe, umbilical cord, umbilical cord blood, amniotic membrane, chorionic membrane, and other placental gelatins, fluids, cells and extracellular material obtained from a seronegative, healthy human.

The use of amniotic membrane, chorionic membrane, or a combination of amniotic and chorionic membranes obtained from human birth tissue to form a tympanic construct are generally provided. The tympanic construct may act to repair a tympanic membrane defect as well as reduce post-operative scar tissue formation, reduce pain, reduce inflammation, and, generally, aid in the healing cascade. Methods for aseptically processing intact amnion and/or chorion membranes to produce a material that may be used to prepare a tympanic construct are also provided.

The amniotic and chorionic membranes may be utilized alone or in various combinations or layers to form the tympanic construct. The term "membrane" refers to an amniotic membrane, a chorionic membrane, or both a chorionic and an amniotic membrane. According to one embodiment, the tympanic construct includes one or more layers including an amniotic membrane. According to another embodiment, the tympanic construct includes one or more layers that include a chorionic membrane. According to yet another embodiment, the tympanic construct includes one or more layers of an amniotic membrane and one or more layers of a chorionic membrane.

According to one embodiment, the tympanic construct includes at least one amniotic membrane, or at least one chorionic membrane, or at least one amniotic membrane and at least one chorionic membrane. In such an embodiment, the membrane(s) is/are not cross-linked. The membrane(s) is/are treated with at least one alcohol composition that includes typically from about 90% to about 100% ethanol. The resulting membrane(s) is/are terminally sterilized to form a tympanic construct.

To obtain human birth tissue material, potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-1 and anti-HTLV-II); and syphilis (a non-treponemal or treponemal-specific assay may be performed).

Human birth tissue is preferably recovered from a full-term aseptic Cesarean delivery of a newborn. Alternatively, human birth tissue is recovered from a full-term vaginal delivery of a newborn. The placental organ, including the placental globe, umbilical cord, associated membranes (chorionic membrane and amniotic membrane), and other gelatins, fluids, cells and extracellular matrix can be recovered from a seronegative, healthy human after the newborn is removed. The placental globe, umbilical cord, and other gelatins, fluids, cells and extracellular matrix can be removed and discarded.

The membrane(s) giving rise to the tympanic construct as described herein may be produced by processing human birth tissue according to the steps provided herein. Processing does not change the physical properties of the resulting membrane to yield the membrane tissue unacceptable for clinical use. Instruments, solutions, and supplies coming into contact with tissue during the processing of the placental tissue are sterile. All surfaces coming in contact with tissue intended for transplant are either sterile or draped using aseptic technique.

Throughout processing, the orientation of the particular membrane is identified to ensure that in use, the correct side of the membrane is placed on or around the tympanic membrane. Either the fetal side or the maternal side of the membrane may be placed on or around the tympanic membrane, depending upon the specific use/procedure and the tympanic construct composition (i.e., the type of membrane (s) used and the number of membrane layers).

Figure 2:
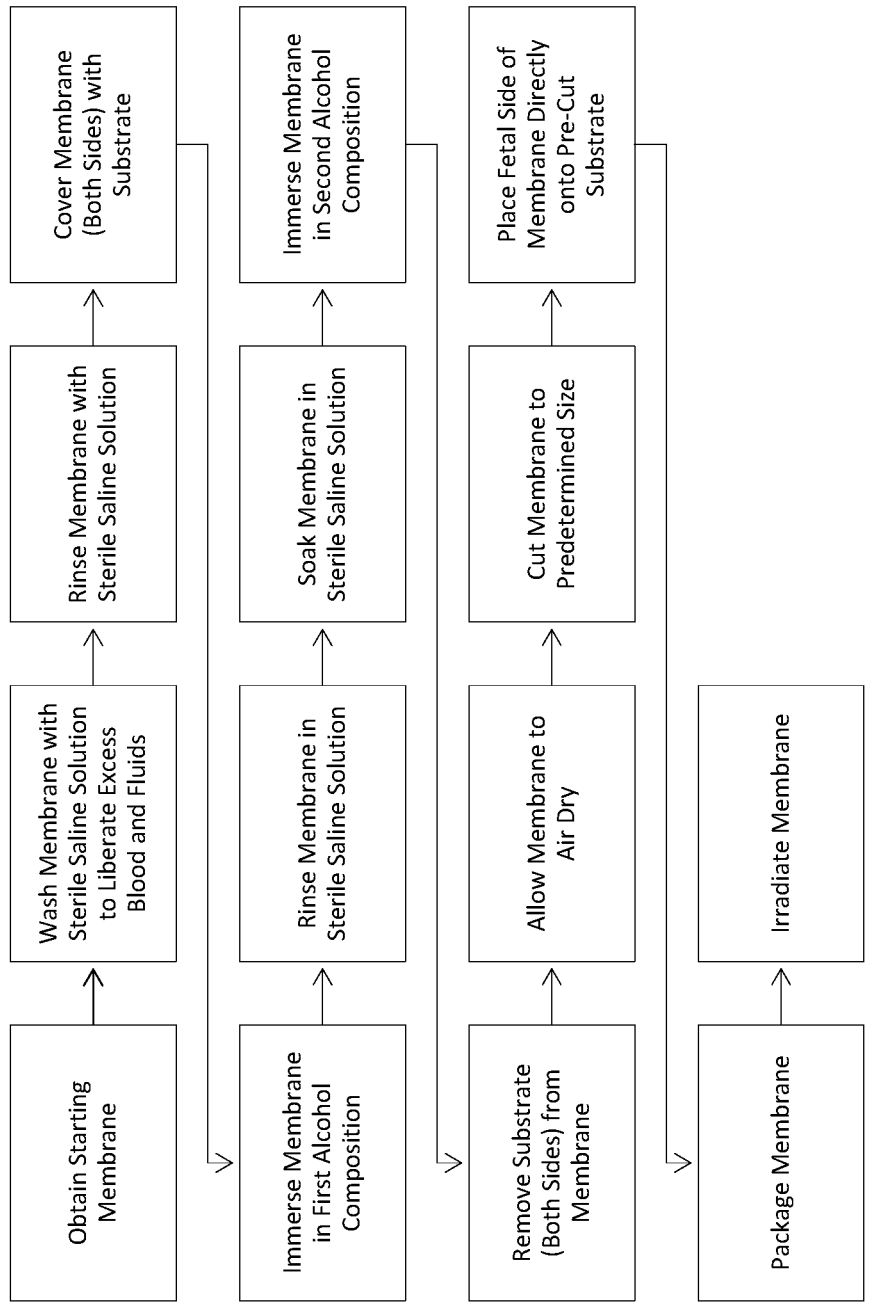
FIG. 2 illustrates a method of preparing a tympanic construct according to one embodiment.

According to the embodiment as illustrated in FIG. 1 or FIG. 2, the tympanic construct is prepared by first obtaining amniotic membrane, chorionic membrane, or both amniotic and chorionic membrane from a seronegative, healthy human via cesarean section or vaginal delivery as described herein. In particular embodiments where only the amniotic membrane is chosen for further processing, the chorionic membrane can be removed by blunt dissection. For example, the chorionic membrane may be removed by applying finger pressure and sliding it off of the amniotic membrane using as little pressure as possible to avoid tearing of the amnion. The chorionic membrane and any excess tissue can be discarded.

The recovered amniotic membrane, chorionic membrane, or both amniotic and chorionic membrane may be initially stored in a sterile saline solution at a temperature between about 1° C. to about 10° C. for a period of up to about five days prior to further processing. According to one embodiment, the sterile saline solution comprises from about 0.9% to about 20% NaCl, preferably 15% NaCl.

Optionally, the membrane(s) may be treated with an oxidizer. In one embodiment, the oxidizer is hydrogen peroxide, which is also used as a sterilant and to enhance the solubilization of lipids. Such a treatment process includes the steps of:

(a) rinsing the membrane with 120 ml of sterile isotonic solution per gram of membrane for a period of up to about ten minutes;

(b) treating the membrane with 60 ml of hydrogen peroxide per gram of membrane for a period of up to about ten minutes; and (c) rinsing the membrane with 120 ml of sterile isotonic solution per gram of membrane for a period of up to about ten minutes.

The membrane is then immersed in a basin containing a sterile saline solution. According to one embodiment, the sterile saline solution includes typically from about 0.9% to about 20% NaCl.

Excess blood and fluids may be liberated from the membrane by gently stirring or swirling the fluid in a circular motion in the basin or by placing the basin on a shaker. The membrane can then be rinsed with a sterile saline solution. In one embodiment, the sterile saline solution includes NaCl in a concentration range of about 0.9% to about 20%. In one embodiment, the membrane may be rinsed in bowls or trays of sufficient size to allow the membrane to be spread out to improve the rinse coverage. Sufficient saline solution is utilized to ensure that the membrane is completely immersed. The saline is then decanted into a discard basin.

Multiple saline rinse cycles may be performed. In one embodiment, the membrane is rinsed for two or more separate rinse cycles, with each rinse cycle lasting for a maximum of five minutes. The membrane is covered with a substrate on both the fetal membrane side and the maternal membrane side. Appropriate substrates include, but are not limited to, sterile mesh or polymer mesh of adequate size and shape for covering each side of the membrane.

According to the embodiment as illustrated in FIG. 2, the membrane may optionally be immersed in an alcohol composition from about 90% to about 100% ethanol (see FIG. 2—referred to as "first alcohol composition"). In certain embodiments, the alcohol composition includes about 95.5% ethanol. In a preferred embodiment, the alcohol composition includes about 100% ethanol.

As illustrated in the embodiment of FIG. 2, the membrane is then optionally rinsed with a sterile saline solution. Alternatively, the membrane is rinsed multiple times with a sterile saline solution. According to one embodiment, the sterile saline solution includes typically from about 0.9% to about 20% of NaCl. According to one embodiment, the rinse step is conducted for a maximum time period of five minutes. The membrane can then be optionally soaked in a sterile saline solution. According to one embodiment, the sterile saline solution includes typically from about 0.9% to about 20% of NaCl. According to one embodiment, soaking is conducted for a maximum period of about 35 minutes.

As illustrated in each of the embodiments of FIGS. 1 and 2, the membrane is immersed in an alcohol composition for a period of typically from about 24 hours to about 384 hours. The alcohol composition includes about 90% to about 100% ethanol. In certain embodiments, the alcohol composition includes about 95.5% ethanol. In a preferred embodiment, the alcohol composition includes about 100% ethanol. Treatment of the membrane within a particular alcohol concentration range for the particular timeframe at this step in the process has yielded unexpected results related to the handling characteristics. One of ordinary skill in the art appreciates the difficulty of handling and manipulating amniotic and chorionic tissue when applied to a specific site. Specifically, existing amniotic and chorionic grafts are difficult to place over a specific site, particularly because these grafts fold back over on themselves ("wrinkling"), rendering proper placement and positioning of the graft at the wound site very challenging. When treated with the aforementioned alcohol composition for the particular timeframe, the resulting tympanic construct exhibits improved handling characteristics in that it does not "wrinkle" and allows for easy placement at the chosen site. Additionally, the membrane is uniquely processed to allow adhesion to the surrounding tympanic membrane tissue without the aid of support materials, tissue glue/adhesives or sutures. Furthermore, the alcohol treatment is multi-functional, providing a means of sterilization, preservation, and chemical dehydration for the membrane, in addition to serving as a radioprotectant for the membrane prior to terminal irradiation.

The substrate can then be removed from both the fetal membrane side and the maternal membrane side. The membrane can then be spread on a flat, dry and sterile surface. The membrane is then allowed to air dry completely at ambient temperature for a period of up to typically about three hours. The membrane can then be cut to the desired size, optionally covered with a substrate, and subsequently packaged. The tympanic construct can be cut into patches of any desired size for a particular application by a rotary type cutting tool. A grooved or similarly indicated cutting board may be used to aid in cutting a straight and correctly sized covering. In another embodiment, the tympanic construct is cut by free hand using a scalpel and ruler to achieve the desired size. The fetal side of the membrane can then be placed directly onto a pre-cut substrate to form a tympanic construct. Suitable substrates include, for example, a gauze or synthetic mesh. The tympanic construct can be packaged in a dry state. Alternately, the tympanic construct can be packaged in sterile water, crystalloids, or another sterilizing, preserving or storage agent, including ethanol. The covering can be removed after the opposing side has been applied to the surgical site. The packaging and covering as disclosed herein can facilitate the handling of the tympanic construct, namely maintaining and identifying the orientation of the fetal and maternal side of the tympanic construct for the user. The packaging may also promote storage of the tympanic construct.

The packaged tympanic construct can be terminally sterilized using irradiation. In one embodiment, an electron beam irradiation is applied in an amount up to about 45 kGy. The sterilized tympanic construct may be stored for up to typically about two years from the date of processing. In one embodiment, the tympanic construct may be stored under proper conditions for as much as about five years following processing. The sterilized tympanic construct may be stored in any container suitable for long-term storage. Preferably, the sterilized tympanic construct is stored in a sterile double peel-pouch package.

The tympanic construct as described herein may be of various sizes, thicknesses, and shapes. The tympanic construct is preferably of sufficient size and shape to be applied onto or around a tympanic membrane defect. The tympanic construct may be any shape or conformation that facilitates the treatment of a portion of the existing tympanic membrane. In certain embodiments, the tympanic construct may be shaped as a square, rectangular, circular or oval, or may be cut to conform generally to the shape of the defect. The thickness of the tympanic construct may vary depending on application, the type of membrane and the number of membrane layers. Typically, the tympanic construct is from about 0.01 µm to about 200 µm thick.

A method of treating a tympanic membrane defect is also provided. Before attempting any correction of the defect, a hearing test can be performed, and the patient can be evaluated for Eustachian tube function, as partial or complete loss of Eustachian tube function can exacerbate a tympanic membrane defect (e.g., puncture) and interfere with the adherence of a construct to the tympanic membrane. The method includes the steps of preparing a tympanic construct as provided herein and placing the tympanic construct on or around a tympanic membrane defect. According to one embodiment, the repair of the tympanic membrane is a tympanoplasty. According to another embodiment, the repair of the tympanic membrane is a myringoplasty. According to either embodiment, the otolaryngologist may approach repair of a tympanic membrane defect either through the auditory canal (trans-canal approach), or via a post-auricular incision followed by folding the ear forward to expose the tympanic membrane (post-auricular approach).

The tympanic membrane defect can be any perforation, tear, abrasion, rupture, puncture wound, or other trauma. Such a defect may be caused accidentally, by trauma, by infection, or may be caused deliberately (e.g., from insertion of one or more tubes allowing drainage of fluids in the middle ear past the tympanic membrane and out the auditory canal (e.g., perforation(s) to allow a myringotomy tube installation, or a perforation caused by surgical removal of diseased or damaged tissue). The defect may be acute, or the defect may be chronic (e.g., in existence for two months or more). In certain embodiments, the defect may be a deformity that has arisen as the result of a disease or infection or was present at birth.

A method of treating a surgical site is also provided. The method includes the steps of preparing a tympanic construct as provided herein and placing the tympanic construct on or around a portion of the tympanic membrane subject to a surgical procedure.

If desired, the one or more membranes forming the tympanic construct utilized in the methods provided herein may be treated, coated or impregnated with one or more of a variety of optional components to aid in defect resolution, healing, and recovery. Exemplary optional components include, but are not limited to, antibiotics, anti-inflammatory agents, anti-viral agents, growth factors, antiproliferative agents, cytokines, antihistamines, pain medications, biocides, cellular attractant and scaffolding reagents, wound healing agents or sealants, nutritional agents (e.g., vitamins), hormones, alkylating agents, immunomodulatory agents (e.g., steroids), and/or other specialized proteins or small molecules. The one or more membranes forming the tympanic construct may be combined with a substrate (sterile gauze, sterile polymer material, or other tissue or biomaterial) to increase the strength of the tympanic construct.

If desired, the one or more membranes forming the tympanic construct may be utilized with at least one composition or device for delivering, fastening or fixing the tympanic construct on or around a tympanic membrane defect. Exemplary compositions include, but are not limited to, tissue glue or tissue adhesive, fibrin glue, fibrinogen glue, hydrogel tissue glue, chondroitin sulfate aldehyde, or natural proteins. Exemplary devices include, but are not limited to, sutures or forceps.

A kit for use by a surgical professional is also provided. According to one embodiment, the kit includes one or more packaged and sterilized tympanic constructs as provided herein. The kit may further include at least one set of instructions. The kit may further include a container adapted to accommodate the aforementioned components while preserving the tympanic construct as per applicable Food and Drug Administration guidelines.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Having generally described the present invention, a further understanding can be obtained by reference to the examples provided herein for purposes of illustration only and are not intended to be limiting.

EXAMPLE 1

Three representative samples of final product for each of three production lots manufactured according to the methods of FIG. 1 were tested for residual ethanol by gas chromatography, analytical method EPA 8260B, CAS No. 64-17-5. Samples were sent to Nelson Laboratories, Inc., 6280 South Redwood Road Salt Lake City, Utah 84123, a GLP qualified microbiology laboratory registered with the FDA and third-party accredited to ISO 17025 standards.

The three samples submitted for testing from production lot #5 (2 cm×3 cm; 2 cm×3 cm; and 1.5 cm×2 cm) included amniotic membranes that had been immersed in an alcohol composition comprising 95.5% ethanol for a period of 110 hours. The three samples submitted for testing from production lot #6 (2 cm×3 cm each) included amniotic membranes that had been immersed in an alcohol composition comprising 95.5% ethanol for a period of 25.5 hours. The three samples submitted for testing from production lot #7 (2 cm×3 cm each) included amniotic membranes that had been immersed in an alcohol composition comprising 95.5% ethanol for a period of 24.9 hours.

Zero headspace extraction was performed with double deionized water as the vehicle extractant. Extraction vessels were tumbled during the entire extraction process. For each of the three production lots, the samples were pooled, and one test article was extracted with a weight of 0.05 g and fluid amount of 50 ml. The starting extraction temperature was 22° C. and the ending extraction temperature was 23° C. The extractions lasted twenty-four hours. All sample extract solutions were observed to be clear and free of particulates. At the end of the extraction period, all test articles were observed to be intact with no observable degradation. Extracts were maintained at room temperature and were not filtered prior to analysis. The vehicle solution was introduced into a purge and trap unit suitable for gas chromatography—mass spectrometry analysis. Control blanks contained no compounds of interest at the reported detection limits. Low level calibration standards were analyzed at the detection levels, and standard percent recoveries were within acceptable method limits. No analytical interferences were observed. All instrument calibration results were within method requirements through all portions of the analysis.

The certificates of analyses for production lots #5, #6 and #7 indicated no detectable amounts of ethanol at the minimum reporting limit (0.5 mg/L). The results are summarized in Table 3 below.

TABLE 3

Ethanol Determination for Production Lots #5, #6 and #7

| Production Lot | Total Time in Ethanol | Weight of Sample | Volume of Fluid | Starting Extraction Temperature | Ending Extraction Temperature | Duration of Extraction | Sample Results |
| --- | --- | --- | --- | --- | --- | --- | --- |
| 5 | 110.0 Hours | 0.05 g | 50 mL | 22° C. | 23° C. | 24 Hours | ND* |
| 6 | 25.5 Hours | 0.05 g | 50 mL | 22° C. | 23° C. | 24 Hours | ND* |
| 7 | 24.9 Hours | 0.05 g | 50 mL | 22° C. | 23° C. | 24 Hours | ND* |

*ND = Not Detected at the Minimum Reporting Limit (0.5 mg/L)

I claim:

1. A tympanic construct comprising:
   at least one chemically dehydrated amniotic membrane, wherein the amniotic membrane is mounted fetal side down on a substrate to form the tympanic construct, and
   wherein the tympanic construct is of sufficient size and shape to be applied onto or around a tympanic membrane defect.

2. The tympanic construct of claim 1, wherein the at least one amniotic membrane is treated with at least one alcohol composition.

3. The tympanic construct of claim 1, wherein the at least one amniotic membrane is terminally sterilized by gamma irradiation or electron beam irradiation.

4. The tympanic construct of claim 1, wherein the tympanic construct is from 0.01 μm to 200 μm thick.

5. The tympanic construct of claim 1, wherein the tympanic membrane defect is selected from the group consisting of perforation, tear, abrasion, rupture, and puncture wound.

6. The tympanic construct of claim 1, wherein the substrate is a sterile gauze substrate or sterile polymer material substrate.

7. A kit for use by a surgical professional comprising:
   one or more packaged and sterilized tympanic constructs according to claim 1; and
   at least one set of instructions.

8. The kit of claim 7, further comprising at least one composition or device for delivering, fastening or fixing the tympanic construct on or around the tympanic membrane defect.

9. The kit of claim 8, wherein the at least one composition is selected from the group consisting of tissue adhesive, fibrin glue, fibrinogen glue, hydrogel tissue glue, chondroitin sulfate aldehyde, and natural proteins.

10. The kit of claim 8, wherein the device is at least one suture.

* * * * *